United States Patent
Anantaneni et al.

(10) Patent No.: US 9,598,358 B2
(45) Date of Patent: *Mar. 21, 2017

(54) ACYLALKYLISETHIONATE ESTERS AND APPLICATIONS IN CONSUMER PRODUCTS

(75) Inventors: Prakasa R. Anantaneni, Austin, TX (US); John Gray, Round Rock, TX (US); Marty J. Renner, Round Rock, TX (US); George A. Smith, Austin, TX (US); David C. Lewis, Austin, TX (US); Donald H. Champion, Pflugerville, TX (US); Christopher J. Whewell, Georgetown, TX (US)

(73) Assignee: HUNTSMAN PETROCHEMICAL LLC, The Woodlands, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/171,039

(22) Filed: Jun. 28, 2011

(65) Prior Publication Data

US 2011/0257072 A1    Oct. 20, 2011

(51) Int. Cl.
| | |
|---|---|
| *C07C 303/32* | (2006.01) |
| *A61K 8/46* | (2006.01) |
| *A61Q 5/02* | (2006.01) |
| *A61Q 19/10* | (2006.01) |
| *C07C 303/02* | (2006.01) |
| *C07C 303/22* | (2006.01) |
| *C07C 309/12* | (2006.01) |
| *C11D 1/28* | (2006.01) |

(52) U.S. Cl.
CPC ............ *C07C 303/32* (2013.01); *A61K 8/466* (2013.01); *A61Q 5/02* (2013.01); *A61Q 19/10* (2013.01); *C07C 303/02* (2013.01); *C07C 303/22* (2013.01); *C07C 309/12* (2013.01); *C11D 1/28* (2013.01)

(58) Field of Classification Search
None
See application file for complete search history.

(56) References Cited

U.S. PATENT DOCUMENTS 5,519,154 A * 5/1996 Naylor ............... C11D 1/28
554/149

FOREIGN PATENT DOCUMENTS

WO    WO 94/09763    * 11/1994

* cited by examiner

*Primary Examiner* — Necholus Ogden, Jr.
(74) *Attorney, Agent, or Firm* — Huntsman International LLC

(57) ABSTRACT

Acylalkylisethionate esters are produced by reacting one or more carboxylic acids with one or more alkyl-substituted hydroxyalkyl sulfonates under esterification reaction conditions. The alkyl-substituted hydroxyalkyl sulfonates used as a raw material in producing the esters are prepared by reacting bisulfate with one or more alkylene oxides. The acylalkylisethionate esters may be used in consumer products.

19 Claims, 3 Drawing Sheets

ACYLALKYLISETHIONATE ESTERS AND APPLICATIONS IN CONSUMER PRODUCTS

CROSS-REFERENCE TO RELATED APPLICATIONS

This application is a divisional of U.S. patent application Ser. No. 10/586,027, which is the National Stage of International Application No. PCT/US04/25968, filed Aug. 11, 2004, which claims benefit of U.S. provisional patent application Ser. No. 60/537,511, filed Jan. 20, 2004. Each of the aforementioned related patent applications is herein incorporated by reference in its entirety.

FIELD OF THE INVENTION

The present invention is directed to the preparation of salts of acylalkylisethionate esters, intermediates in their production, and their application in consumer products.

BACKGROUND OF THE INVENTION

Acylalkylisethionate esters are anionic surfactants that can be used in a variety of personal care cleansers such as soaps, cosmetic compositions, and cleaning formulations. One acylalkylisethionate ester, sodium cocoyl isethionate ("SCI"), is an ester currently used extensively in soap-combi bars (i.e. syndet bars) due to its low solubility in water and mildness (i.e. non-irritating) to the skin as compared to harsher fatty acid soap bars. However, because of its low water solubility, SCI is not suitable for use in liquid cleansers. One method for improving SCI's limited water solubility is to combine SCI with other surfactants such as taurate, amphoacetates and betaines. However, this combination of surfactants still produces a hazy solution that tends to separate during storage. Therefore, it would be desirable to produce acylalkylisethionate esters that are highly water soluble, hydrolytically-stable and non-irritating for use in aqueous as well as non-aqueous consumer products such as personal care cleansers.

SUMMARY OF THE INVENTION

The present invention includes alkyl-substituted hydroxyalkyl sulfonates and methods of preparing alkyl-substituted hydroxyalkyl sulfonates. The alkyl-substituted hydroxyalkyl sulfonates may then be reacted with a carboxylic acid to produce acylalkylisethionate esters. The acylalkylisethionate esters may be used as a surfactant or surface active agent in consumer products such as personal care cleansers. The acylalkylisethionate esters of the present invention are at least as mild to skin as SCI. In addition, unlike SCI, the acylalkylisethionate esters of the present invention are low foaming, highly soluble in water, and hydrolytically stable making the esters easier to handle, store, and compound. Because of their enhanced solubility properties, the alkyl-substituted acylalkylisethionate esters can be dissolved in water or flaked into a fast-dispersing concentrate thus making their use in the formulation of aqueous and non-aqueous consumer products highly desirable.

BRIEF DESCRIPTION OF FIGURES

For a detailed understanding and better appreciation of the present invention, reference should be made to the following detailed description of the invention, taken in conjunction with the accompanying figures.

DETAILED DESCRIPTION

Figure 1:
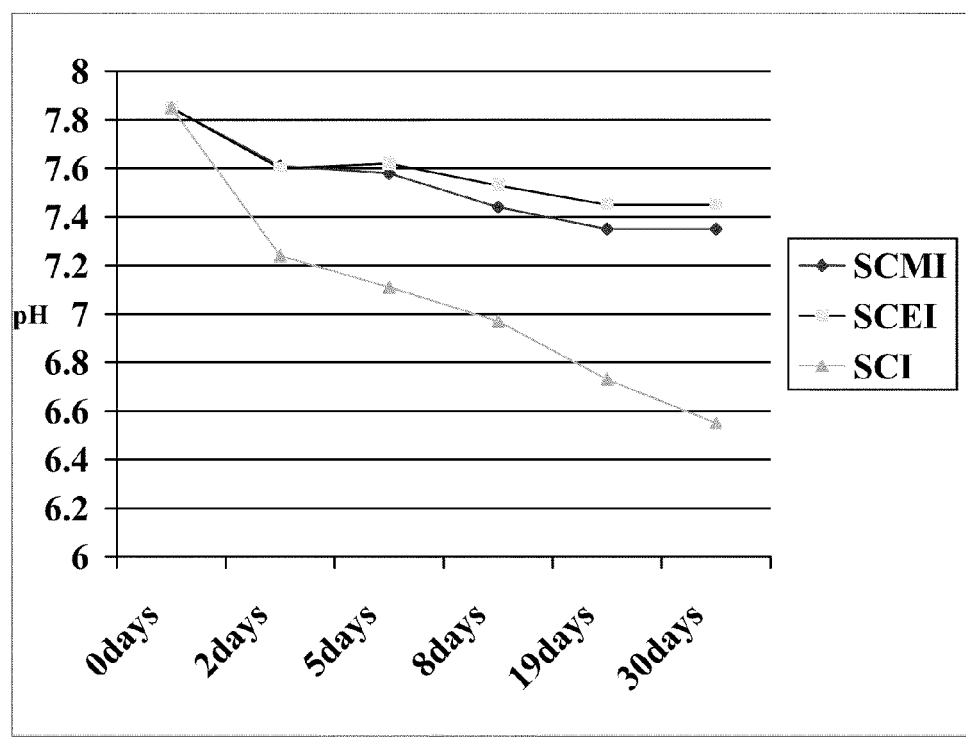
FIG. 1 is a graph depicting the hydrolytic stability of sodium cocoyl isethionate (SCI), sodium cocoyl methyl isethionate (SCMI) and sodium cocoyl ethyl isethionate (SCEI) over a time period of 30 days.

The present invention provides highly soluble, hydrolytically stable, high-tight foaming, mild (i.e. non-irritating) acylalkylisethionate esters useful as a primary or secondary surfactant in aqueous and non-aqueous consumer products such as personal care cleansers. An acylalkylisethionate ester herein refers to an alkyl-substituted acylalkylisethionate ester in which at least one hydrogen on the alkyl chain of the isethionate portion of the molecule is substituted with an alkyl group. That is, an alkyl group is substituted onto at least one carbon atom of the alkane sulfonate portion of the acylalkylisethionate ester. For example, in one embodiment, the alkyl-substituted acylalkylisethionate ester is an alkyl-substituted acylethylisethionate ester having the following general formula (I):

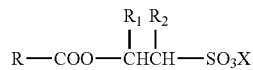

in which R is any hydrocarbon group having between 4 and 25 carbon atoms; $R_1$ and $R_2$ are each independently selected from the group consisting of hydrogen and a branched or straight aliphatic $C_1$ to $C_6$ alkyl group subject to the proviso that only one of $R_1$ and $R_2$ is a branched or straight aliphatic $C_1$ to $C_6$ alkyl group while the remaining $R_1$ or $R_2$ is hydrogen; and X may be any cationic species present for charge neutrality such as hydrogen, an alkali metal such as sodium, potassium and lithium, calcium, magnesium, zinc, aluminum, ammonium and ammonium ions which are substituted with one or more organic groups.

In another embodiment, the alkyl-substituted acylalkylisethionate ester is an alkyl-substituted acylpropylisethionate ester having the general formula (II):

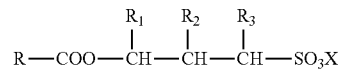

in which R is any hydrocarbon group having between 4 and 25 carbon atoms; $R_1$ and $R_2$ and $R_3$ are each independently selected from the group consisting of hydrogen and a branched or straight aliphatic $C_1$ to $C_6$ alkyl group subject to the proviso that one of $R_1$ and $R_2$ and $R_3$ is a branched or straight aliphatic $C_1$ to $C_6$ alkyl group while the remaining $R_1$ or $R_2$ or $R_3$ is hydrogen; and X may be any cationic species present for charge neutrality such as hydrogen, an alkali metal such as sodium, potassium and lithium, calcium, magnesium, zinc, aluminum, ammonium and ammonium ions which are substituted with one or more organic groups.

The alkyl-substituted acylalkylisethionate esters of the present invention may be prepared by direct esterification of one or more alkyl-substituted hydroxyalkyl isethionates with one or more carboxylic acids. Esterification occurs by mixing alkyl-substituted hydroxyalkyl isethionate with carboxylic acid and optionally an esterification catalyst under esterification conditions. The alkyl-substituted hydroxyalkyl isethionate can be present as the salt of the alkyl-substituted hydroxyalkyl isethionate or in its acidic form. Thus, esterification for one embodiment may occur according to the reaction:

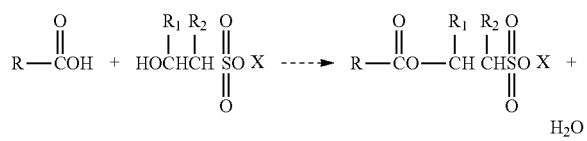

in which R is any hydrocarbon group having between about 4 and about 25 carbon atoms, including straight-chain, branched, saturated, and unsaturated hydrocarbon groups; $R_1$ and $R_2$ may each independently be hydrogen or an alkyl group selected from the group consisting of: $C_1$ to $C_6$ alkyl, subject to the proviso that both $R_1$ and $R_2$ are not simultaneously hydrogen and are not simultaneously both a $C_1$ to $C_6$ alkyl group, and wherein X is a cationic species present for charge neutrality, which may be any cationic species but is preferably selected from the group consisting of: hydrogen, alkali metals, alkaline earth metals, zinc, aluminum, and ammonium ions which are substituted with one or more organic groups, which may be any organic group. When X is hydrogen, the alkyl-substituted alkylisethionic acid is present, which we have surprisingly found to be catalytic during esterification. X can be caused to be present as hydrogen by addition of any strong acid; however, it is most preferable to add the alkyl-substituted alkylisethionic acid itself in its pure form when it is added as an esterification catalyst.

The alkyl-substituted hydroxyalkyl isethionates may be prepared by reacting one or more alkylene oxides with an aqueous solution of bisulfite. The alkylene oxides used in preparing the hydroxyalkyl isethionates may include, for example, propylene oxide, butylene oxide, and any higher alkylene oxides. The concentration of the aqueous solution of bisulfite can range from 10% to 70% by weight and may include any alkali metal aqueous solution of bisulfite such as sodium, potassium or ammonium.

In one embodiment, the alkyl-substituted hydroxyalkyl isethionate is an alky-substituted hydroxyethane sulfonate produced by the following reaction:

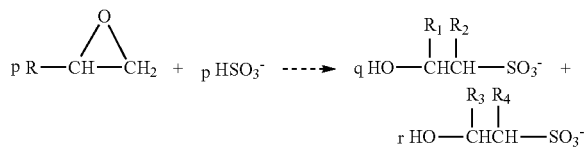

(Replace R with R' above)
where R is a $C_1$ to $C_6$ alkyl group, $R_1$ and $R_2$ are each independently selected from the group of hydrogen and a $C_1$ to $C_6$ alkyl group but only one of $R_1$ and $R_2$ is hydrogen while the other is a $C_1$ to $C_6$ alkyl group; $R_3$ and $R_4$ are each independently selected from the group of hydrogen and a $C_1$ to $C_6$ alkyl group but only one of $R_3$ and $R_4$ is hydrogen while the other is a $C_1$ to $C_6$ alkyl group; and q+r is equal to p. Thus, isomers may be produced during the reaction.

Preferably, one or more cations such as sodium, potassium, lithium, magnesium, calcium, and ammonium ions are present in the aqueous bisulfite solution to maintain charge neutrality, and in fact any ion by which charge neutrality may be accomplished is suitably included in the aqueous solution, including mono-positive ions, di-positive ions, and triply positive ions.

In another embodiment, propylene oxide is reacted with sodium bisulfite to produce sodium 2-methyl 2-hydroxyethane sulfonate and/or sodium 1-methyl 2-hydroxyethane sulfonate or a mixture thereof. In yet another embodiment, butylene oxide is reacted with sodium bisulfite to produce sodium 2-ethyl 2-hydroxyethane sulfonate and/or sodium 1-ethyl 2-hydroxyethane sulfonate or a mixture thereof. In still another embodiment, a mixture of propylene oxide and butylene oxide is reacted with sodium bisulfite to produce sodium 2-methyl 2-hydroxyethane sulfonate, sodium 2-ethyl 2-hydroxyethane sulfonate, sodium 1-methyl 2-hydroxyethane sulfonate, and/or sodium 1-ethyl-2-hydroxyethane sulfonate, or mixtures thereof. The propylene oxide and butylene oxide or ethylene oxide can be combined in any proportion to obtain the desired amounts of each alkyl-substituted hydroxyethane sulfonate.

In producing an acylalkylisethionate ester by the reaction of a carboxylic acid with an alkylisethionate, such as an alkyl-substituted hydroxyethane sulfonate, the carbon atom of the hydroxyethane sulfonate portion of the molecule connected to the oxygen atom of the ester linkage is herein referred to as the "ester link carbon atom." It has been surprisingly found that when the alkylisethionate contains a high degree of ester link carbons that are secondary carbon atoms, the hydrolytic stability of the final acylalkylisethionate ester product is substantially increased. No similar increase in hydrolytic stability has been observed with regards to increasing the secondary carbon content of the other carbon atom bonded directly to the sulfur atom in the alkylisethionate. Therefore, it is highly desirable to produce an alkyl-substituted hydroxyalkyl isethionate that permits an acylalkylisethionate ester produced therefrom to possess as high a degree of ester link carbons which are secondary carbon atoms as possible.

During production of the alkyl-substituted hydroxyalkyl isethionates, the pH of the reaction solution comprising the alkylene oxide and bisulfite may range from about 4.0 to 10.0. However, to minimize side reactions and side products such as diols, the pH of the reaction solution may be maintained within a range from 5.5 to 8.5. Moreover, the pH of the reaction solution may be maintained optimally at a pH of about 7.0 to maximize production of alkyl-substituted hydroxyalkyl isethionates having a high content of secondary ester link carbons. To maintain the pH of the reaction solution at a desired pH range during the entire reaction, a weak acid or buffering acid and/or more bisulfite may be added to the reaction solution as needed.

In other embodiment, the alkyl-substituted hydroxyalkyl isethionates are prepared by making the bisulfite in situ by reacting a hydroxide solution, such as sodium hydroxide, with sulfur dioxide under pressure. The alkoxide can be added concurrently or after to produce the corresponding hydroxyalkyl isethionates and alkyl-substituted hydroxyalkyl isethionates.

Furthermore, the temperature and pressure of the reaction solution during production of the alkyl-substituted hydroxyalkyl isethionates may range from about 50° C. to about 200° C. and from about 10 psi to about 100 psi, respectively. The temperature and pressure of the reaction solution may be held constant during the entire reaction or one or both may be raised or lowered at any time for any time period to produce the desired alkyl-substituted hydroxyalkyl isethionate.

Furthermore, the alkyl-substituted hydroxyalkyl isethionates may be prepared as a liquid or in solid form. For example, the alkyl-substituted hydroxyalkyl isethionates may first be prepared in liquid form then spray dried to a powder form. Thus, in one embodiment the alkyl-substituted hydroxyalkyl isethionates are prepared in liquid form by reacting propylene oxide and/or butylene oxide with sodium bisulfite. The liquid salts of the alkyl-substituted hydroxyalkyl isethionate are then spray dried to their corresponding powder form. The alkyl-substituted hydroxyalkyl isethionate powders have been found to be less hygroscopic and therefore easier to handle than non-alkyl-substituted isethionate powders making their transportation more efficient and less expensive. In addition, use of the alkyl-substituted hydroxyalkyl isethionate powder allows for the elimination of a water removal step that is normally required when using a liquid alkyl-substituted hydroxyalkyl isethionate during direct esterification.

The alkyl-substituted hydroxyalkyl isethionates may then be used as a raw material along with carboxylic acids in producing the alkyl-substituted acylalkylisethionate esters of the present invention. The carboxylic acids employed in producing the esters of the present invention have the general formula (III): R—COOH where R is any hydrocarbon group having between about 4 to about 25 carbon atoms. The R hydrocarbon group can be saturated or unsaturated, and straight-chain or branched. Generally, an excess of carboxylic acid is used in producing the esters of the present invention. Thus, the amount of carboxylic acid used may range from a mole ratio of carboxylic acid to hydroxyalkyl isethionate of 1.3:1 to 1.1:1. However, a mole ratio range of carboxylic acid to hydroxyalkyl isethionate as high as 2:1 to as low as 0.9:1 may be used if desired.

Examples of carboxylic acids suitable for use in the present invention include: coco acid; butyric acid; hexanoic acid; caproic acid; caprylic acid; capric acid; lauric acid; myristic acid; palmitic acid; palmitoleic acid; stearic acid; oleic acid; linoleic acid; arachidic acid; gadoleic acid; arachidonic acid; EPA; behinic acid; eruic acid; DHA; lignoceric acid; naturally occurring fatty acids such as coconut oil, tallow, palm kernel oil, butterfat, palm oil, olive oil, corn oil, linseed oil, peanut oil, fish oil and rapeseed oil; synthetic fatty acids made as chains of a single length or a selected distribution of chain lengths; and mixtures of any of the foregoing.

Those skilled in the art will appreciate that fatty acids obtained from naturally occurring sources are mixtures of acids having various carbon chains of various lengths. Therefore, it is within the scope of this invention to use one or more naturally occurring fatty acids (including mixtures thereof), synthetic fatty acids (including mixtures thereof) and mixtures of both natural and synthetic fatty acids. Moreover, "coco acid" or "coco fatty acid" as used herein is a commercial fatty acid mixture containing a range of carboxylic acids having chain lengths of between about $C_8$ to $C_{18}$, and some saturation which may be removed by hydrogenation. Thus, hydrogenated coco acid is a mixture of carboxylic acids having $C_8$ to $C_{18}$ chain lengths, mostly lauric and myristic, together with some capric and caprylic acids, and contains very little, if any, unsaturation.

To aid in preparation of the alkyl-substituted acylalkylisethionate esters, an esterification catalyst may be employed and combined with the alkyl-substituted hydroxyalkyl isethionate and carboxylic acid. Appropriate esterification catalysts suitable for use include alkylisethionic acids, salts of hydroxyalkane sulfonates, methane sulfonic acid, p-toluene sulfonic acid, inorganic acids such as sulfuric acid, phosphoric acid, phosphorous acid, boric acid or their anhydrides, heavy metal salts such as zinc sulfate, zirconium sulfate, zinc isethionate, zinc citrate, zinc borate, aluminum sulfate, titanium sulfate or tungsten phosphate, metal oxides such as zinc oxide, aluminum oxide, magnesium oxide, cerium oxide, zirconium oxide or lanthanum oxide, and also mixtures of two or more of these catalysts, and soaps formed from heavy metals and metal oxides. The esterification catalyst may be employed in an amount from 0.05 to 2% by weight, preferably from 0.05 to 1% by weight, based on total weight of the reactants.

In one embodiment, the alkyl-substituted acylalkylisethionate ester is prepared using the acidic form of alkyl-substituted hydroxyethane sulfonate as the esterification catalyst. The alkyl-substituted hydroxyethane isethionic acid can be added in its pure form or a strong acid can be added to the reaction mixture containing carboxylic acid and salt of the alkyl-substituted hydroxyethane isethionate to convert the isethionate salt to the acidic form.

The dual use of the alkyl-substituted hydroxyethane sulfonate as both a reactant and a catalyst is preferred since there is no need to quench or to remove the catalyst, there is no catalyst residues so there is minimal change in the molecular weight distribution of the acylalkylisethionate ester, manufacturing capital expenditures are reduced and processing time is decreased.

The acylalkylisethionate esters according to the present invention produced from alkyl-substituted hydroxyalkyl isethionates are much more hydrolytically stable than acylalkylisethionate esters produced from non-alkyl-substituted hydroxyalkyl isethionates, such as SCI. Currently, users of SCI employ a test to determine the hydrolytic stability of SCI by subjecting an aqueous solution of the SCI to an elevated temperature of 55° C. for a time period up to 30 days, during which the degree of hydrolysis of the SCI is determined. As shown in FIG. 1, the present invention alleviates the problem of hydrolysis. FIG. 1 depicts the hydrolytic stability of a 10% aqueous solutions of SCI and acylmethylisethionate esters prepared from coconut fatty acids and methyl-substituted isethionate (made from reacting propylene oxide and sodium bisulfate) and acylethylisethionate esters prepared from coconut fatty acids and ethyl-substituted isethionate over a 30 day period at a temperature of 56° C. We term the ester produced from coconut fatty acids and methyl-substituted isethionate as "sodium cocoyl methylisethionate" or "SCMI" in its abbreviated form. We term the ester produced from coconut fatty acids and ethyl-substituted isethionate as sodium "cocoyl ethylisethionate" or "SCEI". As shown in FIG. 1, the SCI ester undergoes hydrolysis while both the SCMI and SCEI esters are hydrolytically stable over the 30 day period. Furthermore, the SCMI and SCEI ester were completely soluble when added to water thus forming a clear 10% ester solution. In comparison, the 10% SCI solution was cloudy and required heating to solubilize the SCI in water.

Thus, it has been surprisingly found that by substituting hydrogen with $C_1$ to $C_6$ alkyl groups on one or both of the carbon atoms of the ethane sulfonate portion of an acylalkylisethionate ester, hydrolytic stability and water solubility of the acylalkylisethionate ester is drastically improved. That is by providing a $C_1$ to $C_6$ on one or both of the carbon atoms of the isethionic acid (or isethionate salt) raw material used in producing the acylethylisethionate ester, the water solubility and hydrolytic stability of the modified ester is improved. This result is wholly unexpected in view of the common knowledge in the art that increasing the hydrocarbon character of a material generally results in a reduction of water solubility. As a result of this improved solubility and hydrolytic stability, the acylalkylisethionates of the present invention are suitable for use in liquid personal care cleaners and not limited to soap bars.

In general detail, the esterification reaction can be conducted by charging the carboxylic acid, alkyl-substituted hydroxyalkyl isethionate, and optionally the esterification catalyst under atmospheric pressure or vacuum to a reaction vessel. The reaction vessel is flushed thoroughly with dry inert gas, such as nitrogen. Direct esterification is carried out by heating the reaction mixture to the reaction temperature with stirring. The water that may be introduced into the reaction mixture with the starting components and the water that is formed as a result of the esterification reaction is discharged from the reaction vessel. In addition, it may be also be required to distill off some of the excess carboxylic acid during the course of the esterification reaction. The reaction time to complete esterification will vary from 1 to 12 hours depending on the reaction temperature, and if present, the amount of esterification catalyst. The final alkyl-substituted acylalkylisethionate ester product can then be delivered in liquid or solid form, such as a powder or paste, for use as a raw material in the formulation of personal care cleansers.

The esterification reaction may be performed in a reaction vessel under atmospheric pressure. However, to aid in water removal, mild vacuum (500-550 mm Hg) may be applied during commencement of the charging of the reactants or anytime during the reaction. Applying mild vacuum also allows for water removal without distilling of the carboxylic acid. Preferably, the vacuum applied is not allowed to drop below 500 mm Hg so as to prevent carboxylic acid distillation when such is not desired.

Generally, the reaction vessel is heated to a single reaction temperature range. However, the process can employ more than one reaction temperature range. For example, the reaction vessel may be heated to a first reaction temperature range and held at that temperature range for a period of time to remove water, then subsequently heated further to a second temperature range higher than the first and held for a period of time. The reaction temperature ranges employed during the esterification reaction may range from about 200° C. to about 240° C. However, it has been surprisingly found that if alkyl-substituted hydroxyethane isethionic acid is used as the catalyst, the reaction temperature can be lowered to a temperature range of about 90° C. to about 180° C., preferably about 120° C. to about 160° C.

In one embodiment, the acylalkylisethionate ester is produced by combining one or more carboxylic acids and one or more sodium salts of the alkyl-substituted hydroxyalkane isethionate with an alkyl-substituted hydroxyethane isethionic acid catalyst to a reaction vessel. The reaction vessel is purged using nitrogen and the reaction mixture is heated at a first temperature range of about 120° C. to about 130° C. for 30 minutes to remove water from the reaction components. The reaction mixture is then subsequently heated to a range of about 140° C. to about 150° C. to start the esterification reaction. Mild vacuum (500-550 mm Hg) is applied during the esterification reaction to assist in removal of water and the reaction mixture is continually heated until the distilling over of water ceases. The vacuum can be adjusted during the reaction to prevent carboxylic acid from distilling over. After esterification is complete, the residual alkyl-substituted hydroxyethane isethionic acid present as a catalyst may be neutralized with an alkali such as caustic, amine, ammonia or substituted ammonium compounds such as mono-, di-, and triamines, and alkanolamine such as ethanolamine. The excess fatty acid can be conveniently removed by vacuum distillation at temperatures and pressures varying from 100°-250° C. and 1-200 mm Hg to make the product substantially fatty acid free.

Once formed, the acylalkylisethionate esters may be used as a surfactant or surface active agent in a variety of personal care cleansers. Personal care cleansers include, but are not limited to: liquid soaps, shampoos, showergels, bubble baths, synthetic soap-combi-bars, acne washes, anti-dandruff shampoos, make-up removers, facial scrubs, baby wipes and children wipes. Thus, the compounds of the invention may be used in any personal care cleansing composition as may be known to those skilled in the art.

The acylalkylisethionate esters of the present invention may be used in personal care cleansers as a primary surfactant at levels ranging from 1% to 60% by weight. In addition, the acylalkylisethionate esters of the present invention may be blended with other surfactants and materials which are used in personal care cleansers at acylalkylisethionate ester levels ranging up to about 60% by weight. To the extent that other surfactants may be used in combination with the acylalkylisethionate esters of the present invention in forming binary active systems, ternary active systems etc., the acylalkylisethionate ester may comprise the majority of the surface active system (if more than one active is required) in which it is referred to as the primary surfactant, or it may comprise less than the majority of the surface active system in which it is referred to as the secondary surfactant.

Other surfactants and materials which may be used in combination with the alkyl-substituted acylalkylisethionate esters in forming the personal care cleanser include amphoteric/zwitterionic surfactants; anionic surfactants; nonionic surfactants; cationic surfactants; and optional ingredients.

Amphoteric surfactants useful in the invention can broadly be described as a surface active agent containing at least one anionic and one cationic group and can act as either acids or bases depending on pH. Some of these compounds are aliphatic derivatives of heterocyclic secondary and tertiary amines in which the aliphatic radical may be straight or branched and wherein one of the aliphatic substituents contains from about 6 to about 20, preferably 8 to 18, carbon atoms and at least one contains an anionic water-solubilizing group, e.g., carboxy, phosphonate, phosphate, sulfonate, sulfate.

Zwitterionic surfactants can be broadly described as surface active agents having a positive and negative charge in the same molecule which molecule is zwitterionic at all pHs. Zwitterionic surfactants can be best illustrated by betaines and sultaines. The zwitterionic compounds generally contain a quaternary ammonium, quaternary phosphonium or a tertiary sulfonium moiety. The cationic atom in the quaternary compound can be part of a heterocyclic ring. In all of these compounds there is at least one aliphatic group, straight chain or branched, containing from about 6 to 20, preferably 8 to 18, carbon atoms and at least one aliphatic substituent containing an anionic water-solubilizing group, e.g., carboxy, sulfonate, sulfate, phosphate or phosphonate.

Examples of suitable amphoteric and zwitterionic surfactants include the alkali metal, alkaline earth metal, ammonium or substituted ammonium salts of alkyl amphocarboxyglycinates and alkyl amphocarboxypropionates, alkyl amphodipropionates, alkyl monoacetate, alkyl diacetates, alkyl amphoglycinates, and alkyl amphopropionates wherein alkyl represents an alkyl group having from 6 to about 20 carbon atoms. Other suitable surfactants include alkyliminomonoacetates, alkyliminidiacetates, alkyliminopropionates, alkyliminidipropionates, and alkylamphopropylsulfonates having between 12 and 18 carbon atoms, alkyl betaines and alkylamidoalkylene betaines and alkyl sultaines and alkylamidoalkylenehydroxy sulfonates.

Anionic surfactants which may be used in the present invention are those surfactant compounds which contain a long chain hydrocarbon hydrophobic group in their molecular structure and a hydrophilic group, including salts such as carboxylate, sulfonate, sulfate or phosphate groups. The salts may be sodium, potassium, calcium, magnesium, barium, iron, ammonium and amine salts of such surfactants.

Anionic surfactants include the alkali metal, ammonium and alkanol ammonium salts of organic sulfuric reaction products having in their molecular structure an alkyl, or alkaryl group containing from 8 to 22 carbon atoms and a sulfonic or sulfuric acid ester group.

Examples of such anionic surfactants include water soluble salts of alkyl benzene sulfonates having between 8 and 22 carbon atoms in the alkyl group, alkyl ether sulfates having between 8 and 22 carbon atoms in the alkyl group and 2 to 9 moles ethylene oxide in the ether group. Other anionic surfactants that can be mentioned include alkyl sulfosuccinates, alkyl ether sulfosuccinates, olefin sulfonates, alkyl sarcosinates, alkyl monoglyceride sulfates and ether sulfates, alkyl ether carboxylates, paraffinic sulfonates, mono and di alkyl phosphate esters and ethoxylated derivatives, acyl methyl taurates, fatty acid soaps, collagen hydrosylate derivatives, sulfoacetates, acyl lactates, aryloxide disulfonates, sulfosucinamides, naphthalene-formaldehyde condensates and the like. Aryl groups generally include one and two rings, alkyl generally includes from 8 to 22 carbon atoms and the ether groups generally range from 1 to 9 moles of ethylene oxide (EO) and/or PO, preferably EO.

Specific anionic surfactants which may be selected include linear alkyl benzene sulfonates such as decylbenzene sulfonate, undecylbenzene sulfonate, dodecylbenzene sulfonate, tridecylbenzene sulfonate, nonylbenzene sulfate and the sodium, potassium, ammonium, triethanol ammonium and isopropyl ammonium salts thereof.

Nonionic surfactants may also be used in combination with the alkyl-substituted acylalkylisethionate esters of the present invention. The nonionic surfactant(s) is not critical and may be any of the known nonionic surfactants which are generally selected on the basis of compatibility, effectiveness and economy.

Examples of useful nonionic surfactants include condensates of ethylene oxide with a hydrophobic moiety which has an average hydrophilic lipolytic balance (HLB) between about 8 to about 16, and preferably between about 10 and about 12.5. The surfactants include the ethoxylated primary or secondary aliphatic alcohols having from about 8 to about 24 carbon atoms, in either straight or branch chain configuration, with from about 2 to about 40, and preferably between about 2 and about 9 moles of ethylene oxide per mole of alcohol.

Other suitable nonionic surfactants include the condensation products of from about 6 to about 12 carbon atoms alkyl phenols with about 3 to about 30, and preferably between about 5 to about 14 moles of ethylene oxide.

Many cationic surfactants are known in the art and almost any cationic surfactant having at least one long chain alkyl group of about 10 to 24 carbon atoms is suitable for optional use in the present invention.

Other optional ingredients or additives which may be used in combination with alkyl-substituted acylalkylisethionate esters in formulating personal care cleansers include pH adjusting chemicals, for example, lower alkanolamines such as monoethanolamine (MEA) and triethanolamine (TEA). Sodium hydroxide solutions may also be utilized as an alkaline pH adjusting agent. The pH adjusting chemicals function to neutralize acidic materials that may be present. Mixtures of more than one pH adjusting chemical can also be utilized.

Phase regulants (well known liquid detergent technology) may also be optionally used in the present invention. These can be represented by lower aliphatic alcohols having from 2 to 6 carbon atoms and from 1 to 3 hydroxyl groups, ethers of diethylene glycol and lower aliphatic monoalcohols having from 1 to 4 carbon atoms and the like.

Detergent hydrotropes may also be included. Examples of detergent hydrotropes include salts of alkylarylsulfonates having up to 3 carbon atoms in the alkyl group e.g., sodium, potassium, ammonium, and ethanolamine salts of xylene, toluene, ethylbenzene, cumene, and isopropylbenzene sulfonic acids.

Other optional supplemental additives include defoamers such as high molecular weight aliphatic acids, especially saturated fatty acids and soaps derived from them, dyes and perfumes; fluorescent agents or optical brighteners; anti-redeposition agents such as carboxymethyl cellulose and hydroxypropylmethyl cellulose; suspension stabilizing agents and soil release promoters such as copolymers of polyethylene terephthalate and polyoxyethylene terephthalate; antioxidants; softening agents and anti-static agents; photo activators and preservatives; polyacids, suds regulators, opacifiers, bacteriacide, and the like. Suds regulants can illustrated by alkylated polysiloxanes and opacifiers can be illustrated by polystyrene; bactericide can be illustrated by butylated hydroxytoluene.

Although not required, an inorganic or organic builder may optionally be added in small amounts to the final composition. Examples of inorganic builders include water-soluble alkali metal carbonates, bicarbonates, silicates and crystalline and amorphous alumino silicates. Examples of organic builders include the alkali metal, alkaline metal, ammonium and substituted ammonium polyacetates, carboxylates, polycarboxylates, polyacetyl, carboxylates and polyhydroxy sulfonates. One example of a commonly used builder is sodium citrate.

The optional ingredients and optional surfactants can be added to the alkyl-substituted acylalkylisethionate ester before, during or after formulation of the personal care cleanser. In addition, blends of the alkyl-substituted acylalkylisethionate ester in combination with these optional ingredients and surfactants can be made directly for sale or for compounding to meet the needs of the user.

Thus, the acyalkylisethionate esters of the present invention are useful in formulations which contain materials typically used by and known to those skilled in the art as being useful in formulating soap products, detergent products, and other cleansing-like products, particularly, but not limited, to personal care cleansers. For purposes of this invention, the words "material known to those skilled in the art as being useful in formulating soaps, detergents, and the like" means one or more of the materials selected from the group consisting of: fatty acids, alkyl sulfates, ethanolamines, amine oxides, alkali carbonates, water, ethanol, isopropanol, pine oil, sodium chloride, sodium silicate, polymers, alcohol alkoxylates, zeolites, perborate salts, alkali sulfates, enzymes, hydrotropes, dyes, fragrances, preservatives, brighteners, builders, polyacrylates, essential oils, alkali hydroxides, ether sulfates, alkylphenol ethoxylates, fatty acid amides, alpha olefin sulfonates, paraffin sulfonates, betaines, chelating agents, tallowamine ethoxylates, polyetheramine ethoxylates, ethylene oxide/propylene oxide block copolymers, alcohol ethylene oxide/propylene oxide low foam surfactants, methyl ester sulfonates, alkyl polysaccharides, N-methyl glucamides, alkylated sulfonated diphenyl oxide, and water soluble alkylbenzene sulfonates or alkyltoluene sulfonates, as the use of such in formulating soaps, detergents, and the cleansing-like products are known in the art.

In one embodiment, the acylalkylisethionate esters of the present invention may be present in facial and body cleansing compositions. These cleansing compositions may also comprise a fatty acid soap together with other non-soap surfactants, such as mild synthetic surfactants. Body and facial cleaning compositions may also generally include a moisturizer or emollient and polymeric skin feel and mildness aids. The compositions may further optionally include thickeners (e.g., magnesium aluminum silicate, carbopol), conditioners, water soluble polymers (e.g., carboxymethylcellulose), dyes, hydrotropes brighteners, perfumes and germicides.

In another embodiment, the acylalkylisethionate esters of the present invention may be present in a shampoo. The shampoo composition may also comprise one or more other surfactants, a compound considered useful for treating dandruff, such as selenium sulfide, a suspending agent, an amide, nonionic polymer material for aiding in dispersing particles, nonvolatile silicone fluid, and a variety of other nonessential components suitable for rendering the composition more formulatable, such as preservatives, viscosity modifiers, pH adjusting chemicals, perfumes, and dyes.

In still another embodiment, the acylalkylisethionate esters of the present invention may be present in a light duty liquid detergent composition. The light duty liquid detergent composition may further include one or more other surfactants, opacifiers (e.g. ethylene glycol distearate), thickeners (e.g. guar gum), antimicrobial agents, anti-tarnish agents, heavy metal chelators (e.g. EDTA), perfumes and dyes.

In a further embodiment, the acylalkylisethionate ester of the present invention may be present in a heavy duty liquid detergent composition. The heavy duty liquid detergent composition may also include one or more other surfactants, an electrolyte (i.e. water soluble salt), enzymes with or without stabilizers such as calcium ion, boric acid, propylene glycol and/or short chain carboxylic acids, and conventional alkaline detergency builders.

In yet another embodiment, the alkyl-substituted acylalkylisethionate ester may be present in a conditioner composition that comprises alkylamine compounds.

In a different embodiment, the acylalkylisethionate esters of the present invention may be present in a cosmetic composition. The cosmetic composition may further include at least one polymer thickening agent, one or more chemical preservatives or water activity depressants to prevent microbial spoilage, a sun-screening agent such as p-aminobenzoic acid, and a vehicle. The vehicle can include any diluent, dispersant or carrier useful in ensuring an even distribution of the composition when applied to skin and may include water, an emollient such as an alcohol or oil, a propellant for example, trichloromethane, carbon dioxide or nitrous oxide, a humectant, and a powder such as chalk, talc, and starch.

Advantages the alkyl-substituted acylalkylisethionate esters of the present invention have over traditional surfactants include: (1) the high water solubility of the alkyl-substituted acylakylisethionate esters allows the esters to be used alone in aqueous personal care cleansers or other detergent solutions thus not requiring the need for the addition of other costly co-surfactants that are used for solubilizing other acylakylisethionate esters such as SCI; (2) the alkyl-substituted acylalkylisethionate esters are hydrolytically stable in aqueous solutions due to their secondary alcohol ester structure; (3) because of their non-irritating properties, the alkyl-substituted acylakylisethionate esters can be used as a primary surfactant in place of traditional anionic surfactants such as [sodium lauryl sulfate and sodium lauryl ether sulfate] in personal care cleansers; (4) no 1:4 dioxane is made or present during the production of the alkyl-substituted acylalkylisethionate esters; and (5) "sulfate-free" personal care cleansers can be made using the alkyl-substituted acylalkylisethionate esters without requiring the addition of taurates and sarcosinates needed for removing sulfates in current personal care cleansers.

The examples which now follow should be considered exemplary of the present invention, and not delimitive thereof in any way.

EXAMPLE 1

Preparation of Sodium Methyl Isethionate

A 3-gallon stainless steel-316 autoclave reactor was charged with 9.40 pounds of 35% aqueous sodium bisulfite solution having a pH 6.5-7.0 and then nitrogen purged to exclude air. The reactor was then heated to about 70° C. and 1.0 lbs of propylene oxide was added to the reactor at a pressure of 60 p.s.i. The reactants were allowed to react for about 30 minutes at a temperature of about 80° C. after which time the pressure in the reactor dropped to about 1 p.s.i. The reaction was allowed to continue for 60 minutes at 80° C. then cooled to 50° C. and the product solution was removed from the reactor and analyzed. Analysis showed the product solution having a pH of 13.50, <0.50% by weight propylene glycol, and both the 2-methyl, 2-hydroxy ethane 1-sulfonate and 1-methyl 2-hydroxy ethane 1-sulfonate isomers present.

A second 3-gallon stainless steel-316 autoclave reactor was charged with 9.69 pounds of 35% aqueous sodium bisulfite solution having a pH 6.5-7.0 and then nitrogen purged to exclude air. The reactor was heated to about 70° C. and 1.5 lbs of propylene oxide was added to the reaction at a pressure of 60 p.s.i. The reactants were allowed to react at 80° C. for 30 minutes after which time the pressure dropped to about 1 p.s.i. The reaction was allowed to continue for 60 minutes at a temperature of 95° C. then cooled to 50° C. and the product solution was removed from the reactor and analyzed. Analysis showed the product solution having a pH of 14.00, about 3.0% by weight propylene glycol, and both the 2-methyl, 2-hydroxy ethane 1-sulfonate and 1-methyl 2-hydroxy ethane 1-sulfonate isomers present.

In a 170-gallon stainless steel-316 reactor equipped with an agitator, nitrogen line, oxide line, temperature probe and a pH probe, was charged with 300 pounds of DI water and 120 lbs of 50% caustic solution. The reactor was pressure purged with nitrogen three times (40-0 psig). $S_{O2}$ was then passed through the reactor and solution with stirring to a pH of 7.0-7.50. The reactor was then heated to about 70°-75° C. and propylene oxide was added to the reactor at a rate of 0.50 lb/minute. The pH during the reaction controlled addition by the addition of small injections of $S_{O2}$. Furthermore, the addition of PO was slowed towards the end of the reaction to maintain good pH control. The reactants were allowed to digest at 95° C. for 4 hours. A total of 93 lbs of $S_{O2}$ and 90 lbs of propylene oxide were used during the entire reaction. The reactor was then opened to fume hood and stripped of any unreacted propylene oxide with a nitrogen purge for one hour. The reaction mixture was cooled to room temperature and discharged into drums. The clear and colorless product was analyzed and the results showed: 0.50% by weight propylene glycol and 50.20% by weight sodium methyl isethionate (with both 2-methyl, 2-hydroxy ethane 1-sulfonate and 1-methyl, 2-hydroxy ethane 1-sulfonate isomers present).

EXAMPLE 2

Preparation of Sodium Ethyl Isethionate

A 3-gallon stainless steel-316 autoclave reactor was charged with 9.69 pounds of 35% aqueous sodium bisulfite solution having a pH 6.5-7.0 and then nitrogen purged to exclude air. The reactor was then heated to about 70° C. and 2.6 lbs butylene oxide was added to the reactor at a pressure of 60 p.s.i. The reactants were allowed to react for about 30 minutes at a temperature of about 80° C. after which time the pressure in the reactor dropped to about 1 p.s.i. The reaction was allowed to continue for 60 minutes at 95° C. then cooled to 50° C. and the product solution was removed from the reactor. Upon cooling, shiny crystalline plates separated out of the product solution requiring water be added to dissolve the solids back into solution. The product solution was then analyzed and analysis showed the product solution having a pH of 14.00, about 3.0% by weight butylene glycol, and both the 2-ethyl, 2-hydroxy ethane 1-sulfonate and 1-ethyl 2-hydroxy ethane 1-sulfonate isomers present.

A second 3-gallon stainless steel-316 autoclave reactor was charged with 9.69 pounds of 35% aqueous sodium bisulfite solution having a pH 5.0-5.5 and then nitrogen purged to exclude air. The reactor was heated to about 70° C. and 2.6 lbs of butylene oxide was added to the reaction at a pressure of 60 p.s.i. The reactants were allowed to react at 80° C. for 30 minutes after which time the pressure dropped to about 1 p.s.i. The reaction was allowed to continue for 60 minutes at a temperature of 95° C. then cooled to 50° C. and the product solution was removed from the reactor. Upon cooling, shiny crystalline plates separated out of the product solution requiring water be added to dissolve the solids back into solution. The product solution was then analyzed and analysis showed the product solution having a pH of 14.00, about 13.0% by weight butylene glycol, and both the 2-ethyl, 2-hydroxy ethane 1-sulfonate and 1-ethyl 2-hydroxy ethane 1-sulfonate isomers present.

EXAMPLE 3

Preparation of Sodium Cocoyl ($C_8$ to $C_{18}$) Methyl Isethionate Ester

A laboratory reactor (500 ml round bottom flask equipped with mechanical stirrer, addition funnel, condenser, thermocouple and gas sparging provision) was initially charged with 212 grams (0.98 moles) of a carboxylic acid (hydrogenated coco acid C-110, P&G Chemicals, Cincinnati, Ohio). Also added to the reactor was a total of 165 grams (1.0 moles) of sodium methyl isethionate containing a mixture of the sodium salts of 2-methyl, 2-hydroxy ethane 1-sulfonate and 1-methyl, 2-hydroxy ethane 1-sulfonate. 5.00 grams of the corresponding zinc methylisethionate, in the same isomer proportions as above, was added as a catalyst. The reactor was flushed thoroughly with dry nitrogen and heated to 120°-130° C. for 30 minutes to remove water from the alkyl-substituted sodium methyl isethionate. The temperature of the reactor contents was then raised to 200° C. for 6 hours after which time excess fatty acid is removed by distillation under vacuum at 10 mm Hg to acceptable fatty acid levels (<10%) and the product mixture contains 80% by weight of the corresponding esters suitable for blending into a personal care cleansing composition.

In a second laboratory reactor (500 ml round bottom flask equipped with mechanical stirrer, addition funnel, condenser, thermocouple, and gas sparging provision) was added 131.5 grams (0.625 moles) of a carboxylic acid (Coconut fatty acid C-110, P&G Chemicals, Cincinnati, Ohio), a total of 82.5 grams (0.5 moles solids) of sodium methyl isethionate containing a mixture of the sodium salts of 2-methyl, 2-hydroxy ethane 1-sulfonate and 1-methyl 2-hydroxy ethane 1-sulfonate, and 2.2 grams of zinc citrate as a catalyst. The reactor is flushed thoroughly with dry nitrogen and the solution heated at 220° C. for 6 hours after which time excess fatty acid is removed by distillation under vacuum at 10 mm Hg to acceptable fatty acid levels (<10%) and the product solution is cooled to 160° C.-170° C. The product solution is removed from the reactor and analyzed and the results showed a product containing 81.5% by weight of the corresponding esters suitable for blending into a personal care cleansing composition, 12.0% by weight unreacted carboxylic acid, and 3.9% by weight unreacted sodium methyl isethionate.

EXAMPLE 4

Preparation of Sodium Capryloyl/Caproyl ($C_8$ to $C_{10}$) Methyl Isethionate Ester In a laboratory reactor (500 ml round bottom flask equipped with mechanical stirrer, addition funnel, condenser, thermocouple, and gas sparging provision) was charged 118 grams (0.75 moles) of a carboxylic acid (fatty acid C810, P&G Chemicals, Cincinnati, Ohio) and to the reactor was added a total of 82 grams (0.5 moles solids) of sodium methyl isethionate containing a mixture of the sodium salts of 2-methyl, 2-hydroxy ethane 1-sulfonate and 1-methyl 2-hydroxy ethane 1-sulfonate. 2.2 grams of zinc citrate was added to the mixture as a catalyst. The reactor was flushed thoroughly with dry nitrogen and the reactants heated at 220° C. for 6 hours after which time the product is cooled to 160° C.-170° C. The product solution is removed from the reactor and analyzed and the results showed the white solid had a saponification value of 186, actives by two phase titration 2.54 meq/g and containing 86.7% by weight of the corresponding esters suitable for blending into a personal care cleansing composition, 6.7% by weight unreacted carboxylic acid, and 6.5% by weight unreacted sodium methyl isethionate.

EXAMPLE 5

Preparation of Sodium Caproyl ($C_{10}$) Methyl Isethionate Ester

In a laboratory reactor (500 ml round bottom flask equipped with mechanical stirrer, addition funnel, condenser, thermocouple, and gas sparging provision) was charged 108 grams (0.625 moles) of a carboxylic acid (fatty acid C-1095, P&G Chemicals, Cincinnati, Ohio) and to the reactor is added a total of 82.5 grams (0.5 moles solids) of sodium methyl isethionate containing a mixture of the sodium salts of 2-methyl, 2-hydroxy ethane 1-sulfonate and 1-methyl 2-hydroxy ethane 1-sulfonate. 1.9 grams of zinc citrate was added to the mixture as a catalyst. The reactor is flushed thoroughly with dry nitrogen and the reactants heated to 220° C. for 6 hours after which time the product is cooled to 160° C.-170° C. The product solution is removed from the reactor and analyzed and the resulting white solid contained 82.5% by weight of the corresponding ester suitable for blending into a personal care cleansing composition, 7.7% by weight unreacted carboxylic acid, and 7.4% by weight unreacted sodium methyl isethionate.

EXAMPLE 6

Preparation of Sodium Lauroyl ($C_{12}$) Methyl Isethionate Ester

In a laboratory reactor (500 ml round bottom flask equipped with mechanical stirrer, addition funnel, condenser, thermocouple, and gas sparging provision) was charged 125 grams (0.625 moles) of a carboxylic acid (fatty acid C1299, P&G Chemicals, Cincinnati, Ohio) and to the reactor was added a total of 83 grams (0.5 moles solids) of sodium methyl isethionate containing a mixture of the sodium salts of 2-methyl, 2-hydroxy ethane 1-sulfonate and 1-methyl 2-hydroxy ethane 1-sulfonate. 2.2 grams of zinc citrate was added to the mixture as a catalyst. The reactor is flushed thoroughly with dry nitrogen and the reactants heated to 220° C. for 6 hours after which time the product solution is cooled to 160° C.-170° C. The resulting white solid is removed from the reactor and analyzed and the results showed a product containing 82.0% by weight of the corresponding ester suitable for blending into a personal care cleansing composition, 15.6% by weight unreacted carboxylic acid, and 3.9% by weight unreacted sodium methyl isethionate.

EXAMPLE 7

Preparation of Sodium Cocoyl ($C_{12}$-$C_{18}$) Methyl Isethionate Ester

In a laboratory reactor (500 ml round bottom flask equipped with mechanical stirrer, addition funnel, condenser, thermocouple, and gas sparging provision) was charged 137.5 grams (0.625 moles) of a carboxylic acid (fatty acid Emery 627, Henkel Corp., Emery Group, Cincinnati, Ohio) and to the reactor was added a total of 85 grams (0.5 moles solids) of sodium methyl isethionate (95% by weight) containing a mixture of the sodium salts of 2-methyl, 2-hydroxy ethane 1-sulfonate and 1-methyl 2-hydroxy ethane 1-sulfonate. 1.2 grams of zinc citrate was added to the mixture as a catalyst. The reactor is flushed thoroughly with dry nitrogen and the reactants heated to 220° C. for 6 hours after which time the product solution is cooled to 160° C.-170° C. The white solid is removed from the reactor and analyzed and the results showed a product containing 82.2% by weight of the corresponding esters suitable for blending into a personal care cleansing composition, and 7.9% by weight unreacted carboxylic acid.

EXAMPLE 8

Foaming Tests

Foaming tests were performed using a one-liter capped rotating measuring cylinder foam machine at a rate of 30 revolutions per minute and ambient temperature ranging from about 20° C. to about 22° C. and at a concentration of 0.5% of total surfactants. Foam heights in the graduated cylinder were measured at the start and at 10 minutes of rotation. The results are shown below in Table I:

TABLE I

| Sample | Ingredients (% By Weight) | Foam Height at 0 minutes | Foam Height at 10 minutes | Foam Appearance |
|---|---|---|---|---|
| 1 | 80% sodium lauryl sulfate 20% CAPB* | 250 | 238 | Open Foam |
| 2 | 100% sodium laureth sulfate** | 200 | 170 | Open Foam |
| 3 | 80% sodium laureth sulfate 20% CAPB* | 260 | 220 | Open Foam |
| 4 | 100% SCMI*** | 190 | 160 | Creamy, Tight |
| 5 | 80% SCMI*** 20% CAPB* | 190 | 180 | Creamy, Tight |

*Cocoamidopropyl Betaine (EMPIGEN ® BS/FA)
**EMPICOL ® ESA
***SCMI produced from $C_8$ to $C_{18}$ whole coco fatty acid Sample 1 is a commercial product example having one of the highest flash foam levels in the personal care industry and was used as an internal standard throughout these tests.

The results of this foam test show that the foaming of the $C_8$ to $C_{18}$ SCMI alone is not quite as good as SLES alone, but it still shows synergy with CAPB betaine. This synergy is similar to other anionic surfactants as shown by the results for Sample 5 when 20% by weight SCMI is replaced with CAPB. Thus, SCMI can be used with other surfactants and still maintain excellent foaming properties. The SCMI also shows a consistently tighter, creamier foam as it has smaller bubble size than SLES in these types of formulations.

A second foaming test was performed using the same parameters as above, but a stripped coco fatty acid chain SCMI was tested in place of a whole coco fatty acid chain SCMI. The results of this test are shown in Table II:

TABLE II

| Sample | Ingredients (% By Weight) | Foam Height at 0 minutes | Foam Height at 10 minutes | Foam Appearance |
|---|---|---|---|---|
| 1 | 80% sodium lauryl sulfate 20% CAPB* | 250 | 235 | Open Foam |
| 2 | 100% sodium lauryl sulfate | 255 | 245 | Open Foam |
| 3 | 100% SCMI** | 205 | 205 | Creamy, tight |
| 4 | 75% SCMI** 25% CAPB* | 220 | 215 | Creamy, Tight |
| 5 | 82% SCMI*** 18% CAPB* | 230 | 230 | Creamy, Tight |

*Cocoamidopropyl Betaine (EMPIGEN ® BS/FA)
**SCMI produced from $C_{12}$ to $C_{18}$ stripped coco fatty acid Again, the results of this foam test show that foaming can be significantly increased when using a stripped coco fatty acid feed SCMI instead of whole coconut. The $C_{12}$ to $C_{18}$ SCMI flash foam height, as well as the stability at 10 minutes, are better than SLES alone and are similar to SLES/betaine performance. Furthermore, the $C_{12}$ to $C_{18}$ SCMI is again synergistic with CAPB as shown by the results for Samples 4 and 5 when 25% and 18% by weight of SCMI is replaced with CAPB. Thus, SCMI can be used with other surfactants and still maintain or improve excellent foaming properties.

Figure 2A:
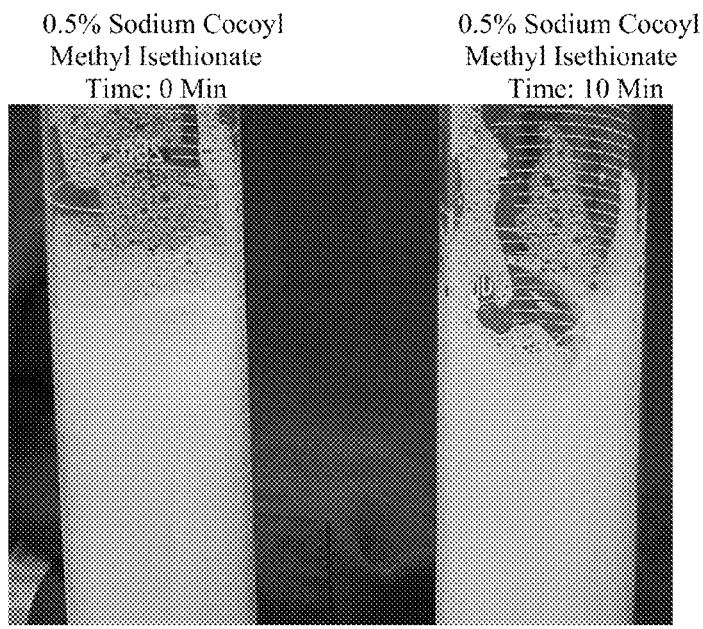
FIG. 2A depicts the foaming characteristics of SCMI.
Figure 2B:
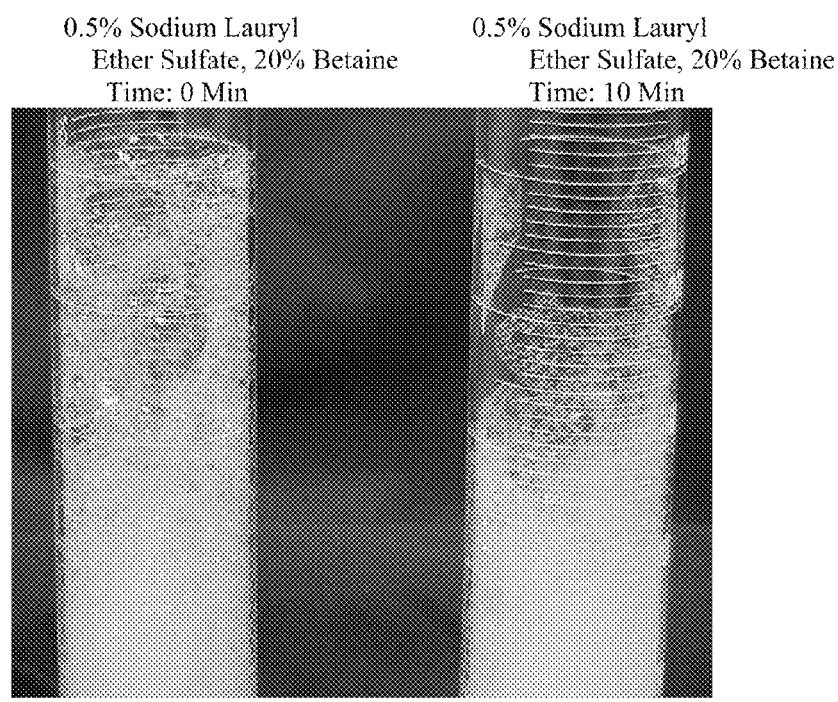
FIG. 2B depicts the foaming characteristics of sodium lauryl ether sulfate (SLES) and sodium lauryl sulfate (SLS)

Finally, as shown in FIGS. 2A and 2B, the foam appearance of SCMI is tighter and creamier than SLES or SLS based cleansers making the use of SCMI in personal care cleansers highly desirable. All samples shown in FIGS. 2A and 2B are at 0.5% active of surfactant.

EXAMPLE 9

Zein Irritation Score

To evaluate the mildness of the products of the present invention, Zein scores were determined for a variety of sulfate and isethionate surfactants and their scores are reported in Table III:

TABLE III

| Product | Zein Score |
| --- | --- |
| Sodium Lauryl Sulfate | 527 |
| Sodium Cocoyl Isethionate | 254 |
| Sodium Cocoyl Methyl Isethionate | 147 |
| Sodium Cocoyl Ethyl Isethionate | 104 |
| Sodium Lauroyl Isethionate | 160 |
| Sodium Lauroyl Methyl Isethionate | 134 |
| Sodium Lauroyl Ethyl Isethionate | 187 |

From these in vitro results, the methyl and ethyl isethionates of the present invention are expected to be less irritating and therefore milder than sodium cocoyl isethionate which has been noted in the literature to be a non-skin irritant and eye irritant at levels of 10% by weight.

EXAMPLE 10

Use of Sodium Cocoyl Methyl Isethionate as a Primary Surfactant in High Foaming Personal Cleansers An SCMI Concentrate can be produced by directly adding the molten SCMI produced, such as in Example 3, into a solution of water and betaines (e.g. EMPIGEN® BS/FA, Huntsman Corporation, Austin, Tex.). If the SCMI is in a powder or flaked form, the SCMI Concentrate may be formed by dissolving the SCMI powder or flakes in a solution containing cold water and betaines.

The SCMI Concentrate that is formed is a white pearlescent solution having a viscosity ranging from 3000-5000 cps. The SCMI Concentrate is easy to handle and its physical properties are similar to sodium laureth sulfate (e.g. EMPICOL®, Huntsman Corporation, Austin, Tex.) allowing for its use in existing manufacturing facilities without the need for equipment upgrades.

As shown in Table IV, the SCMI Concentrate can be formulated as follows:

TABLE IV

SCMI Concentrate Formulation

| Ingredient | Amount (% By Weight) |
| --- | --- |
| SCMI | 24.0 |
| CAPB* | 17.0 |
| DMDM Hydantoin 55%** | 0.4 |
| Water | q.s. to 100.0 |

*EMPIGEN® BS/FA

The SCMI Concentrate can be used in the formulation of a variety of personal care cleansers as shown in Tables V to XI.

TABLE V

Simple Economic Shampoo Formulation

| Ingredient | Amount (% By Weight) |
| --- | --- |
| SCMI | 8.0 |
| CAPB* | 2.0 |
| Sodium laureth sulfate** | 1.8 |
| DMDM Hydantoin 55% | 0.4 |
| Water | q.s. to 100.0 |

*EMPIGEN® BS/FA
**EMPICOL® ESB

TABLE VI

Low Irritation Shampoo Formulation

| Ingredient | Amount (% By Weight) |
| --- | --- |
| SCMI | 5.0 |
| Disodium Lauroamphoacetate* | 2.8 |
| Polysorbate 80 | 4.9 |
| DMDM Hydantoin 55% | 0.4 |
| Water | q.s. to 100.0 |

*EMPIGEN® CDL60P

TABLE VII

Baby Shampoo Formulation

| Ingredient | Amount (% By Weight) |
| --- | --- |
| SCMI | 4.0 |
| Disodium Lauroamphoacetate* | 3.0 |
| Polysorbate 80 | 5.9 |
| DMDM Hydantoin 55% | 0.4 |
| Water | q.s. to 100.0 |

*EMPIGEN® CDL60P

TABLE VIII

Luxurious Liquid Soap Formulation

| Ingredient | Amount (% By Weight) |
| --- | --- |
| SCMI | 6.7 |
| Disodium Lauroamphoacetate* | 2.5 |
| CAPB** | 2.5 |
| DMDM Hydantoin 55% | 0.4 |
| Water | q.s. to 100.0 |

*EMPIGEN® CDL60P
**EMPIGEN® BS/FA

TABLE IX

Economic Liquid Soap Formulation

| Ingredient | Amount (% By Weight) |
| --- | --- |
| SCMI | 4.9 |
| Disodium Lauroamphoacetate* | 3.0 |
| CAPB** | 2.2 |

TABLE IX-continued

Economic Liquid Soap Formulation

| Ingredient | Amount (% By Weight) |
|---|---|
| DMDM Hydantoin** | 0.4 |
| Water | q.s. to 100.0 |

*EMPIGEN ® NHSSA
**EMPIGEN ® BS/FA

TABLE X

Showergel Formulation

| Ingredient | Amount (% By Weight) |
|---|---|
| SCMI | 10.2 |
| Sodium laureth sulfate* | 3.9 |
| CAPB** | 2.5 |
| DMDM Hydantoin 55% | 0.4 |
| Water | q.s. to 100.0 |

*EMPICOL ® ESB70
**EMPIGEN ® BS/FA

TABLE XI

Concentrated Showergel Formulation

| Ingredient | Amount (% By Weight) |
|---|---|
| SCMI | 12.0 |
| Sodium laureth sulfate* | 4.0 |
| CAPB** | 2.5 |
| DMDM Hydantoin 55% | 0.4 |
| Water | q.s. to 100.0 |

*EMPICOL ® ESB70
**EMPIGEN ® BS/FA

All formulations produced above using SCMI as the primary surfactant form a clear solution that is hydrolytically stable when stored. In comparison, when SCMI is replaced with SCI as the primary surfactant, the formulations are cloudy and separate when stored. Therefore, the use of SCMI as a primary surfactant in personal care cleansers is desirable since it is highly soluble, hydrolytically stable and mild to the skin.

EXAMPLE 11

Solubility in Taurate

To determine the solubility of SCI, SCMI and SCEI in taurate, three solutions were prepared at ambient temperature. The solutions were formulated to each contain one of SCI, SCMI and SCEI and each contained the following ingredients as shown in Table XII:

TABLE XII

Solubility in Taurate

| Ingredient | Solution 1 (% By Weight) | Solution 2 (% By Weight) | Solution 3 (% By Weight) |
|---|---|---|---|
| SCI | 12.5 | 0 | 0 |
| SCMI | 0 | 12.5 | 0 |
| SCEI | 0 | 0 | 12.5 |
| Disodium | 3.7 | 3.7 | 3.7 |
| Lauroamphoacetate* | | | |
| Sodium Methyl Cocoyl Taurate | 9 | 9 | 9 |
| Sodium Xylene Sulfonate | 0.8 | 0.8 | 0.8 |
| Propylene Glycol | 1.9 | 1.9 | 1.9 |
| DMDM Hydantoin 55% | 0.22 | 0.22 | 0.22 |
| Water | q.s. to 100.0 | q.s. to 100.0 | q.s. to 100.0 |

*EMPIGEN ® CDL60P

Figure 3:
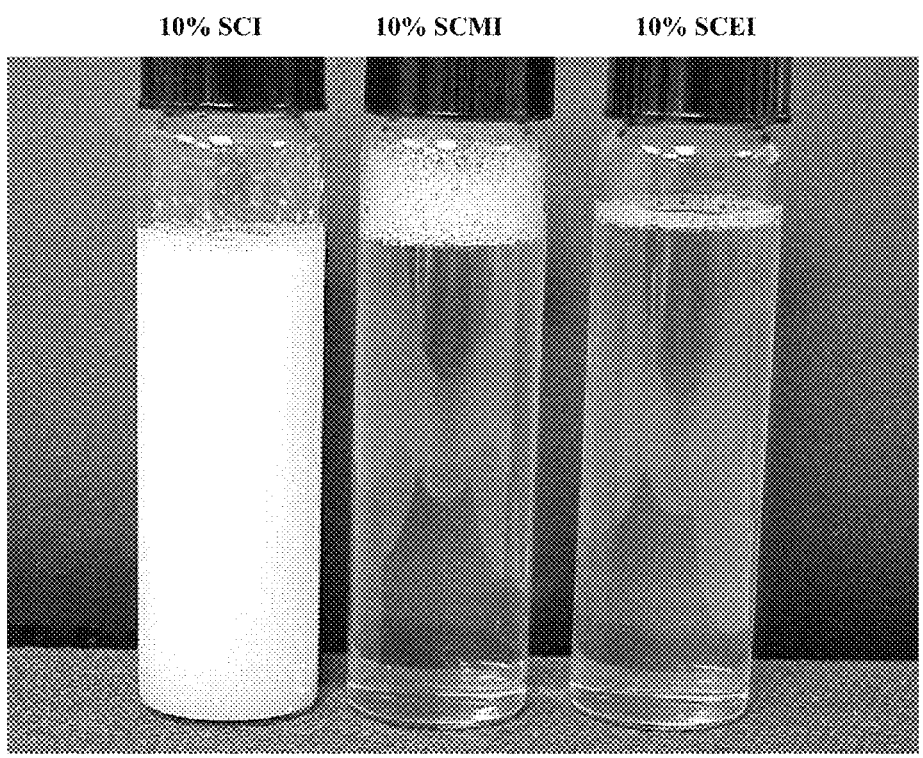
FIG. 3 depicts the solubility of solutions containing one of SCI, SCMI and SCEI.

As shown in FIG. 3, upon formulation, the SCMI solution (Solution 2) and SCEI solution (Solution 3) produce a crystal clear solution and thus are completely soluble. Moreover, the SCMI and SCEI solutions do not separate upon storage. In comparison, the SCI solution (Solution 1) forms a milky cloudy solution that subsequently separates during storage.

Consideration must be given to the fact that although this invention has been described and disclosed in relation to certain preferred embodiments, obvious equivalent modifications and alterations thereof will become apparent to one of ordinary skill in this art upon reading and understanding this specification and the claims appended hereto. The present disclosure includes the subject matter defined by any combination of any one of the various claims appended hereto with any one or more of the remaining claims, including the incorporation of the features and/or limitations of any dependent claim, singly or in combination with features and/or limitations of any one or more of the other dependent claims, with features and/or limitations of any one or more of the independent claims, with the remaining dependent claims in their original text being read and applied to any independent claim so modified. This also includes combination of the features and/or limitations of one or more of the independent claims with the features and/or limitations of another independent claim to arrive at a modified independent claim, with the remaining dependent claims in their original text being read and applied to any independent claim so modified. Accordingly, the presently disclosed invention is intended to cover all such modifications and alterations, and is limited only by the scope of the claims which follow, in view of the foregoing and other contents of this specification. Throughout this specification, various percentages have been set forth and these percentages all refer to percent by weight, unless set forth to the contrary.

What is claimed is:

1. A process useful for forming an aqueous composition of matter having a mixture of alkyl-substituted hydroxyethane sulfonates comprising the steps of:
   a) providing an alkylene oxide having between 3 and 8 carbon atoms per molecule;
   b) providing an aqueous solution comprising bi-sulfite anions;
   c) contacting the aqueous solution with the alkylene oxide while maintaining the pH at a range between about 6.0 and about 10.0,
wherein the mixture of alkyl-substituted hydroxyethane sulfonates comprises:
   (i) a first anion having the structure:

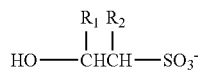

wherein $R_1$ is a straight chain or branched $C_1$ to $C_6$ alkyl group and $R_2$ is hydrogen; and (ii) a second anion having the structure:

wherein $R_4$ is a straight chain or branched $C_1$ to $C_6$ alkyl group and $R_3$ is hydrogen.

2. The process of claim 1, wherein the aqueous solution of bi-sulfite ions further includes at least one ion selected from the group consisting of: sodium, potassium, lithium, magnesium, calcium, and ammonium ions.

3. The process of claim 1, wherein the contacting is conducted at a temperature range of between about 20° C. to about 200° C.

4. The process of claim 1, wherein the contacting is conducted at a pressure range of between about 0.5 atmospheres and about 7 atmospheres.

5. The process of claim 1, wherein the bi-sulfite anions are produced by reacting sulfur dioxide with a hydroxide solution.

6. The process of claim 5, wherein the hydroxide solution is a 50% by weight sodium hydroxide solution.

7. The process of claim 1, wherein the alkylene oxide is selected from the group consisting of: propylene oxide, butylene oxide, and mixtures thereof.

8. The process of claim 7, wherein the aqueous solution of bi-sulfite ions further includes at least one ion selected from the group consisting of: sodium, potassium, lithium, magnesium, calcium, and ammonium ions.

9. The process of claim 1, wherein the pH is maintained at a range between about 7.0 and about 8.0.

10. A process for forming a powder comprising a mixture of sodium alkyl-substituted hydroxyethane sulfonates comprising the steps of:
    a) providing an alkylene oxide having between 3 and 8 carbon atoms per molecule;
    b) providing an aqueous solution of sodium bi-sulfite;
    c) contacting the aqueous solution of sodium bi-sulfite with the alkylene oxide, while maintaining the pH at a range of between about 6.0 and 10.0 for about 1 hour to about 6 hours to form a product mixture; and
    d) drying the product mixture to the powder,
wherein the mixture of sodium alkyl-substituted hydroxyethane sulfonates comprises:
    (i) a first sodium alkyl-substituted hydroxyethane sulfonate having the structure:

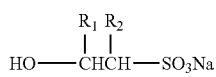

and (ii) a second sodium alkyl-substituted hydroxyethane sulfonate having the structure:

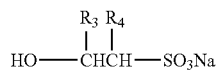

wherein $R_1$ is independently selected from the group consisting of: methyl and ethyl; $R_2$ is hydrogen; $R_3$ is hydrogen; and $R_4$ is independently selected from the group consisting of: methyl and ethyl.

11. The process of claim 10, wherein the contacting is conducted at a temperature range of between about 20° C. to about 200° C.

12. The process of claim 10, wherein the contacting is conducted at a pressure range of between about 0.5 atmospheres and about 7 atmospheres.

13. The process of claim 10, wherein the alkylene oxide is selected from the group consisting of: propylene oxide, butylene oxide, and mixtures thereof.

14. A process for producing a surfactant material useful as a component of a personal care cleansing composition which comprises:
    a) providing a mixture of isethionate anions which comprises
        (i) a first anion having the structure:

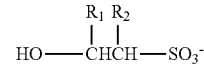

in which $R_1$ is straight chain or branched $C_1$ to $C_6$ alkyl group and $R_2$ is hydrogen; and
        (ii) a second anion having the structure:

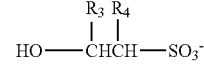

in which $R_3$ is hydrogen and $R_4$ is an straight chain or branched $C_1$ to $C_6$ alkyl group;
    b) contacting the mixture of isethionate anions with one or more carboxylic acids of the formula:

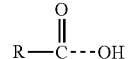

in which R is any hydrocarbon group having between about 4 and about 25 carbon atoms, including straight-chain, branched, saturated and unsaturated hydrocarbon groups so as to form a reactive mixture; and
    c) heating the reactive mixture at any temperature in the range of between 90° C. and 240° C. to produce an acyl alkylisethionate mixture containing at least two different anions which are isethionate esters of a carboxylic acid wherein the mixture of isethionate anions is formed by:
        i) providing an alkylene oxide having between 3 and 8 carbon atoms per molecule;
        ii) providing an aqueous solution of sodium bi-sulfite;
        iii) contacting the aqueous solution of sodium bi-sulfite with the alkylene oxide, while maintaining the pH at a range of between about 6.0 and 10.0 for about 1 hour to about 6 hours to form the mixture of isethionate anions.

15. The process of claim 14, further comprising the step applying a vacuum of about 1 mm Hg to about 200 mm Hg at a temperature of about 100° C. to about 200° C. to reduce the amount of carboxylic acid in the surfactant material to less than 10% by weight.

16. The process of claim 14, wherein $R_1$ is independently selected from the group consisting of: methyl and ethyl; and $R_4$ is independently selected from the group consisting of: methyl and ethyl.

17. The process of claim 14, wherein the contacting is conducted at a temperature range of between about 20° C. to about 200° C.

18. The process of claim 14, wherein the contacting is conducted at a pressure range of between about 0.5 atmospheres and about 7 atmospheres.

19. The process of claim 14, wherein the alkylene oxide is selected from the group consisting of: propylene oxide, butylene oxide, and mixtures thereof.

* * * * *